(12) United States Patent
Kurokawa

(10) Patent No.: US 9,924,924 B2
(45) Date of Patent: Mar. 27, 2018

(54) PIEZOELECTRIC DEVICE, AND ULTRASONIC DEVICE, AS WELL AS PROBE, AND ELECTRONIC APPARATUS

(71) Applicant: SEIKO EPSON CORPORATION, Tokyo (JP)

(72) Inventor: Kenichi Kurokawa, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 440 days.

(21) Appl. No.: 14/813,906

(22) Filed: Jul. 30, 2015

(65) Prior Publication Data

US 2016/0035963 A1    Feb. 4, 2016

(30) Foreign Application Priority Data

Jul. 31, 2014    (JP) .................. 2014-155714

(51) Int. Cl.
| | | |
|---|---|---|
| *H01L 41/09* | (2006.01) | |
| *H01L 41/04* | (2006.01) | |
| *G01S 15/89* | (2006.01) | |
| *A61B 8/00* | (2006.01) | |
| *G01S 7/52* | (2006.01) | |
| *B06B 1/06* | (2006.01) | |
| *H01L 41/08* | (2006.01) | |

(52) U.S. Cl.
CPC .......... *A61B 8/4483* (2013.01); *A61B 8/4427* (2013.01); *B06B 1/067* (2013.01); *B06B 1/0629* (2013.01); *G01S 7/52079* (2013.01); *H01L 41/08* (2013.01)

(58) Field of Classification Search
CPC ... A61B 8/4483; A61B 8/4427; B06B 1/0629; B06B 1/067; G01S 7/52079; H01L 41/08
See application file for complete search history.

(56) References Cited

U.S. PATENT DOCUMENTS

| | | | |
|---|---|---|---|
| 6,972,510 B2 | 12/2005 | Klee et al. | |
| 2012/0306316 A1 | 12/2012 | Nakamura et al. | |
| 2016/0035963 A1* | 2/2016 | Kurokawa ........... | A61B 8/4483 367/7 |

FOREIGN PATENT DOCUMENTS

| | | | | |
|---|---|---|---|---|
| CN | 105310715 A | * | 2/2016 | ........... A61B 8/4483 |
| JP | 2000-244030 A | | 9/2000 | |
| JP | 2000-294844 A | | 10/2000 | |
| JP | 2002-271897 A | | 9/2002 | |
| JP | 2008-137123 A | | 6/2008 | |
| JP | 2012-253405 A | | 12/2012 | |
| JP | 2013-247221 A | | 12/2013 | |
| JP | 2016033937 A | * | 3/2016 | ........... A61B 8/4483 |

* cited by examiner

*Primary Examiner* — Daniel Pihulic

(57) ABSTRACT

A piezoelectric device includes a base, a vibration film, and a piezoelectric element. The base of the piezoelectric device has at least one opening. The opening is closed by the vibration film. The piezoelectric element is located on the vibration film. The vibration film includes a first layer that is has lower water permeability than silicon oxide and a second layer that is in close contact with the first layer and that has a larger toughness value than the first layer.

18 Claims, 8 Drawing Sheets

EMBODIMENT

COMPARATIVE EXAMPLE

PIEZOELECTRIC DEVICE, AND ULTRASONIC DEVICE, AS WELL AS PROBE, AND ELECTRONIC APPARATUS

CROSS-REFERENCE TO RELATED APPLICATIONS

This application claims priority to Japanese Patent Application No. 2014-155714 filed on Jul. 31, 2014. The entire disclosure of Japanese Patent Application No. 2014-155714 is hereby incorporated herein by reference.

BACKGROUND

Technical Field

The present invention relates to a piezoelectric device, an ultrasonic device including the piezoelectric device, and a probe, an electronic apparatus, an ultrasonic imaging apparatus, and the like using the ultrasonic device.

Related Art

In ultrasonic transducers, an opening is formed in a base made of silicon. The opening is closed by a vibration film. A piezoelectric element is supported on a surface of the vibration film. A barrier layer is laminated on the surface of the vibration film. The barrier layer is sandwiched between the piezoelectric element and the vibration film. The barrier layer prevents a chemical interaction between the piezoelectric element and the vibration film. The vibration film may be formed of silicon oxide, silicon carbide, silicon nitride, or other silicon-based materials. The barrier layer may be formed of $Al_2O_3$, $ZrO_2$, $TiO_2$, $HfO_2$, MgO, or $LaAlO_2$. JP-A-2002-271897 is an example of related art.

As in the case where, for example, an acoustic matching material is filled in the opening, water and moisture may enter the opening. In this case, in a space within the opening, the vibration film is exposed to water and moisture. Since silicon oxide has water permeability, water and moisture permeates the vibration film and reaches the piezoelectric element. Consequently, there is a fear that the piezoelectric material may corrode.

SUMMARY

According to a first aspect of the invention, a piezoelectric device includes a base, a vibration film, and a piezoelectric element. The base has at least one opening. The vibration film closes the opening. The piezoelectric element is located on the vibration film. The vibration film includes a first layer and a second layer that is in close contact with the first layer. The first layer has lower water permeability than silicon oxide. The second layer has a larger toughness value than the first layer.

According to another aspect of the invention, the base has a plurality of openings including the opening, and the first layer is continuous between adjacent ones of the openings.

According to another aspect of the invention, the vibration film further includes a third layer that is provided closer to the opening than the first layer and the second layer are and that has an etching rate different from an etching rate of the base.

According to another aspect of the invention, the second layer contains $ZrO_2$.

According to another aspect of the invention, the first layer contains at least one of $Al_2O_3$, TaOx, and HfOx.

According to another aspect of the invention, the third layer contains $SiO_2$.

According to another aspect of the invention, the second layer is formed of $ZrO_2$, the first layer is formed of $Al_2O_3$, and the first layer is arranged such that the first layer is sandwiched between the second layer and the third layer.

According to a second aspect of the invention, an ultrasonic device includes the piezoelectric device according to the aspects described above.

According to a third aspect of the invention, a probe includes the ultrasonic device according to the second aspect, and a housing that supports the ultrasonic device.

According to a fourth aspect of the invention, an electronic apparatus includes the ultrasonic device according to the second aspect and a processor connected to the ultrasonic device and configured to process an output from the ultrasonic device.

According to a fifth aspect of the invention, an ultrasonic imaging apparatus includes the ultrasonic device according to the second aspect and a display device configured to display an image generated based on an output from the ultrasonic device.

According to a sixth aspect of the invention, a piezoelectric device includes a base, a protective film, a vibration film, and a piezoelectric element. The base has an opening. The protective film is provided on the base. The vibration film includes a first layer and a second layer that are laminated on the protective film in an order of the first layer and the second layer. The piezoelectric element is provided on the vibration film. The piezoelectric element is provided in a position at which the piezoelectric element overlaps the opening when viewed in a thickness direction of the base. The first layer has lower water permeability than the protective film. The second layer has a toughness value that is larger than a toughness value of the first layer.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following describes embodiments of the invention with reference to the attached drawings. It should be noted that the embodiments to be described hereinafter are not intended to unduly limit the scope of the invention defined by the claims and that not all of the configurations to be described in the embodiments are necessarily essential as the means for achieving the invention.

(1) Overall Configuration of Ultrasonic Diagnostic Apparatus

Figure 1:
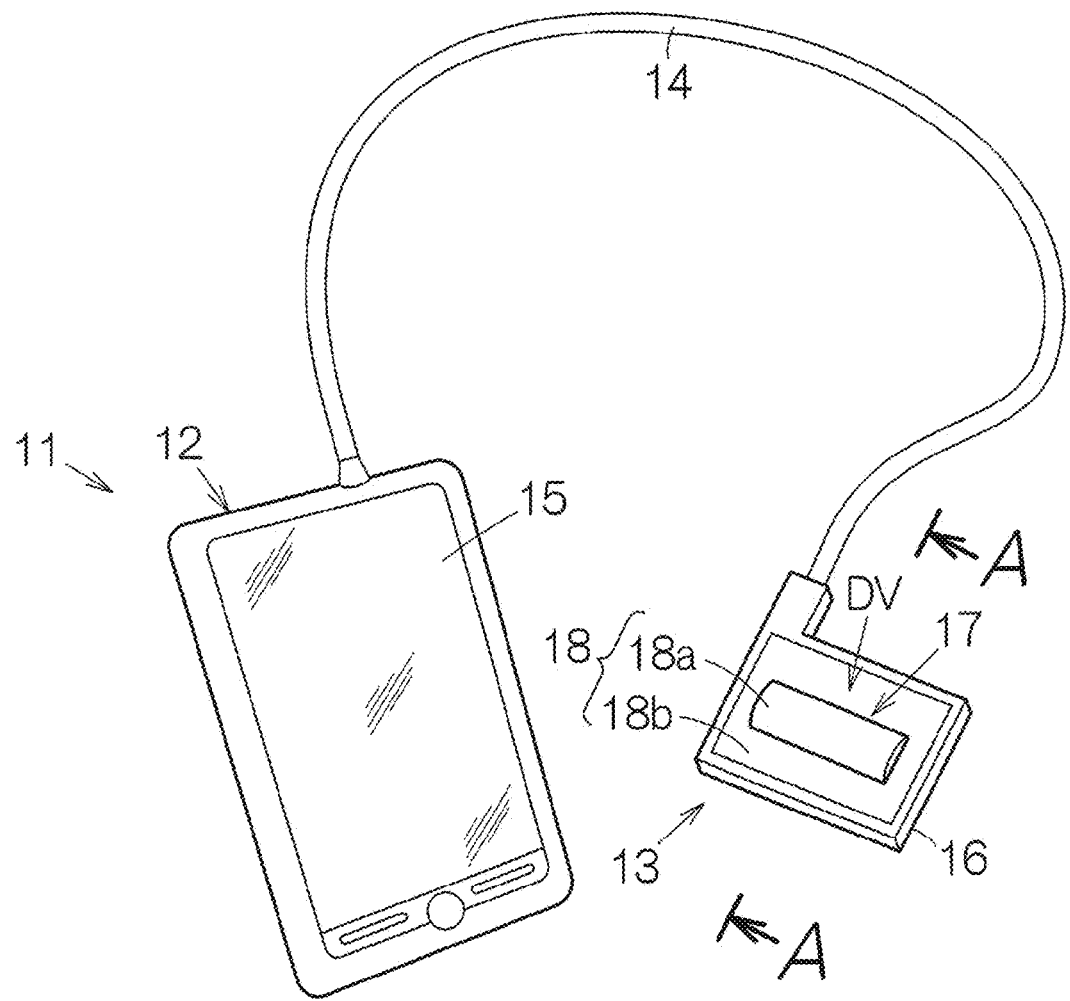
FIG. 1 is an external view showing a specific example, that is, an ultrasonic diagnostic apparatus, of an electronic apparatus according to an embodiment.

FIG. 1 schematically shows the configuration of a specific example, that is, an ultrasonic diagnostic apparatus (ultrasonic imaging apparatus) 11, of an electronic apparatus according to an embodiment. The ultrasonic diagnostic apparatus 11 includes a device terminal (processing unit) 12 and an ultrasonic probe (probe) 13. The device terminal 12 and the ultrasonic probe 13 are connected to each other via a cable 14. Electric signals are transmitted through the cable 14 between the device terminal 12 and the ultrasonic probe 13. A display panel (display device) 15 is incorporated into the device terminal 12. A screen of the display panel 15 is exposed at a surface of the device terminal 12. In the device terminal 12, an image is generated based on ultrasonic waves detected by the ultrasonic probe 13. The imaged detection result is displayed on the screen of the display panel 15.

The ultrasonic probe 13 has a housing 16. An ultrasonic device unit DV is fitted in the housing 16. The ultrasonic device unit DV includes an ultrasonic device (piezoelectric device) 17. The ultrasonic device 17 includes an acoustic lens 18. A partial cylindrical surface 18a is formed on an outer surface of the acoustic lens 18. The partial cylindrical surface 18a is surrounded by a flat plate portion 18b. The entire outer perimeter of the flat plate portion 18b is continuously joined to the housing 16. Thus, the flat plate portion 18b functions as a portion of the housing. The acoustic lens 18 may be formed of, for example, a silicone resin. The acoustic lens 18 has an acoustic impedance that is similar to the acoustic impedance of a living body. The ultrasonic device 17 outputs ultrasonic waves from its surface and receives reflected waves of the ultrasonic waves.

(2) Configuration of Ultrasonic Device According to First Embodiment

Figure 2:
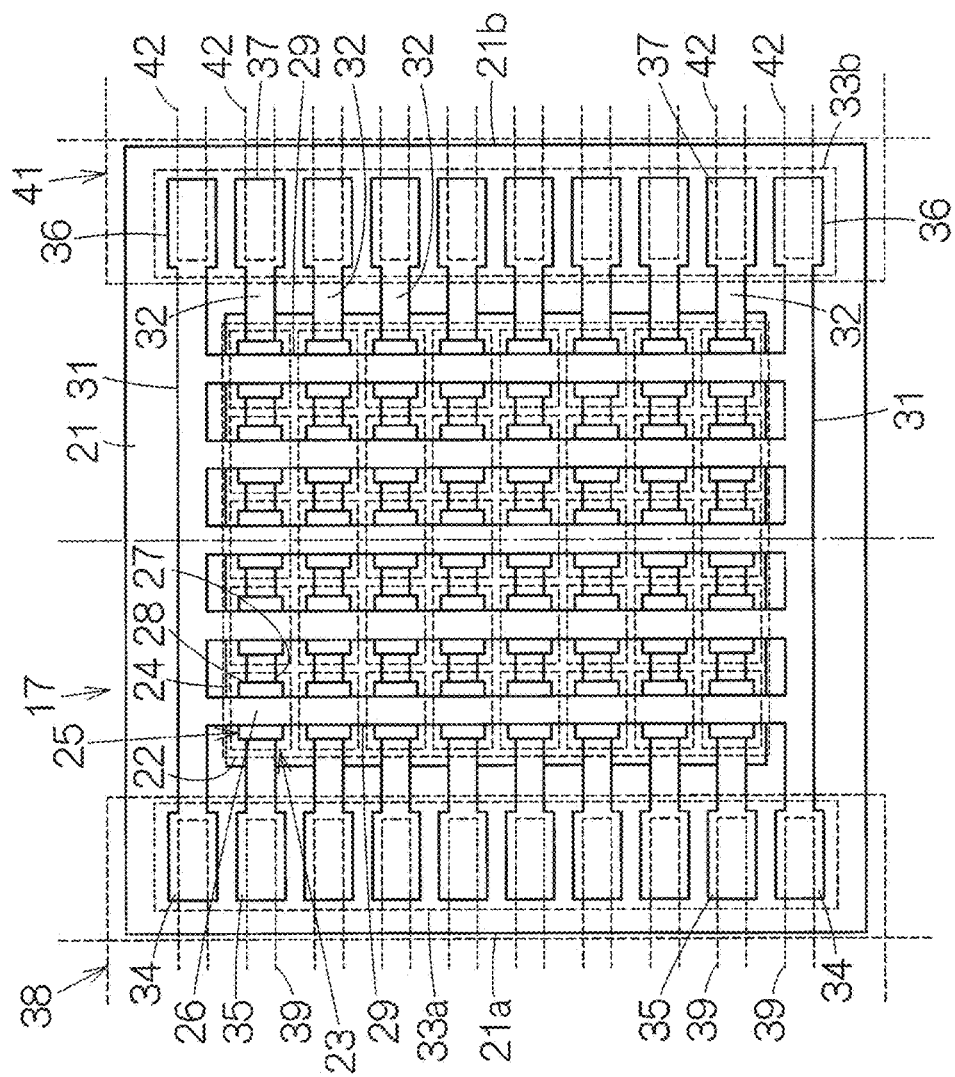
FIG. 2 is an enlarged plan view of an ultrasonic device according to a first embodiment.

FIG. 2 schematically shows a plan view of the ultrasonic device 17. The ultrasonic device 17 includes a base (device substrate) 21. An element array 22 is formed on a surface (first surface) of the base 21. The element array 22 is constituted by an arrangement of thin-film ultrasonic transducer elements (hereinafter referred to as "elements") 23 that are arranged in an array. The arrangement is in the form of a matrix having a plurality of columns and a plurality of rows. The arrangement may also be established as a staggered arrangement. In a staggered arrangement, a group of elements 23 in even rows can be displaced relative to a group of elements 23 in odd rows by one-half of the column pitch. One of the number of elements in a single odd row and the number of elements in a single even row may be smaller than the other by one.

Each element 23 includes a vibration film 24. In FIG. 2, the outline of the vibration film 24 when viewed from above in a direction perpendicular to the film surface of the vibration film 24 (when viewed from above in a thickness direction of the substrate) is shown by dashed lines. A piezoelectric element 25 is formed on the vibration film 24. The piezoelectric element 25 is composed of a top electrode 26, a bottom electrode 27, and a piezoelectric film 28. For each element 23, the piezoelectric film 28 is sandwiched between the top electrode 26 and the bottom electrode 27. The bottom electrode 27, the piezoelectric film 28, and the top electrode 26 are laid one on top of another in that order. The ultrasonic device 17 is configured as a single ultrasonic transducer element chip (substrate).

A plurality of first electric conductors 29 are formed on the surface of the base 21. The first electric conductors 29 extend parallel to one another in a column direction of the arrangement. One first electric conductor 29 is assigned to corresponding one column of elements 23. One first electric conductor 29 is connected commonly to the piezoelectric films 28 of the respective elements 23 that are lined up in the column direction of the arrangement. The first electric conductor 29 forms the top electrodes 26 for the individual elements 23. Both ends of the first electric conductor 29 are connected to a pair of extraction interconnects 31. The extraction interconnects 31 extend parallel to each other in a row direction of the arrangement. Accordingly, all of the first electric conductors 29 have the same length. Thus, the top electrodes 26 are connected commonly to the elements 23 of the entire matrix. The first electric conductors 29 can be formed of, for example, iridium (Ir). However, other electrically conductive materials may also be used for the first electric conductors 29.

A plurality of second electric conductors 32 are formed on the surface of the base 21. The second electric conductors 32 extend parallel to one another in the row direction of the arrangement. One second electric conductor 32 is assigned to corresponding one row of elements 23. One second electric conductor 32 is connected commonly to the piezoelectric films 28 of the respective elements 23 that are lined up in the row direction of the arrangement. The second electric conductor 32 forms the bottom electrodes 27 for the individual elements 23. For example, a laminated film composed of titanium (Ti), iridium (Ir), platinum (Pt), and titanium (Ti) can be used for the second electric conductors 32. However, other electrically conductive materials may also be used for the second electric conductors 32.

Energization of the elements 23 is switched on a row-by-row basis. A linear scan and a sector scan can be achieved in accordance with this switching of energization. Since the elements 23 in a single row simultaneously output ultrasonic waves, the number of elements in a single row, that is, the number of columns of the arrangement can be determined in accordance with the output level of ultrasonic waves. The number of columns can be set at, for example, about 10 to 15. In FIG. 2, some columns are not shown, and only five columns are shown. The number of rows of the arrangement can be determined in accordance with the extent of the scan range. The number of rows can be set at, for example, 128 or 256. In FIG. 2, some rows are not shown, and only eight rows are shown. The functions of the top electrodes 26 and the bottom electrodes 27 may be reversed. That is to say, it is also possible that while the bottom electrodes are connected commonly to the elements 23 of the entire matrix, the top electrodes are connected commonly to the elements 23 in each row of the arrangement.

The outline of the base 21 has a first side 21a and a second side 21b that are defined by a pair of mutually parallel straight lines and that oppose each other. A first terminal array 33a in a single line is disposed between the first side 21a and the outline of the element array 22. A second terminal array 33b in a single line is disposed between the second side 21b and the outline of the element array 22. The first terminal array 33a can form a single line parallel to the first side 21a. The second terminal array 33b can form a single line parallel to the second side 21b. The first terminal array 33a is constituted by a pair of top electrode terminals 34 and a plurality of bottom electrode terminals 35. Similarly, the second terminal array 33b is constituted by a pair of top electrode terminals 36 and a plurality of bottom electrode terminals 37. One top electrode terminal 34 and one top electrode terminal 36 are respectively connected to the two ends of the single extraction interconnect 31. It is sufficient if the extraction interconnects 31 and the top electrode terminals 34 and 36 are formed plane-symmetrically with respect to a perpendicular plane that bisects the element array 22. One bottom electrode terminal 35 and one bottom electrode terminal 37 are respectively connected to the two ends of the single second electric conductor 32. It is sufficient if the second electric conductors 32 and the bottom electrode terminals 35 and 37 are formed plane-symmetrically with respect to a perpendicular plane that bisects the element array 22. Here, the base 21 is formed to have a rectangular outline. The outline of the base 21 may also be square or may be trapezoidal.

A first flexible printed wiring board (hereinafter referred to as "first wiring board") 38 is connected to the base 21. The first wiring board 38 covers the first terminal array 33a. Electrically conductive lines, namely, first signal lines 39 are formed at one end of the first wiring board 38, individually corresponding to the top electrode terminals 34 and the bottom electrode terminals 35. The first signal lines 39 are individually opposed to the top electrode terminals 34 and the bottom electrode terminals 35 and individually joined thereto. Similarly, a second flexible printed wiring board (hereinafter referred to as "second wiring board") 41 covers the base 21. The second wiring board 41 covers the second terminal array 33b. Electrically conductive lines, namely, second signal lines 42 are formed at one end of the second wiring board 41, individually corresponding to the top electrode terminals 36 and the bottom electrode terminals 37. The second signal lines 42 are individually opposed to the top electrode terminals 36 and the bottom electrode terminals 37 and individually joined thereto.

Figure 3:
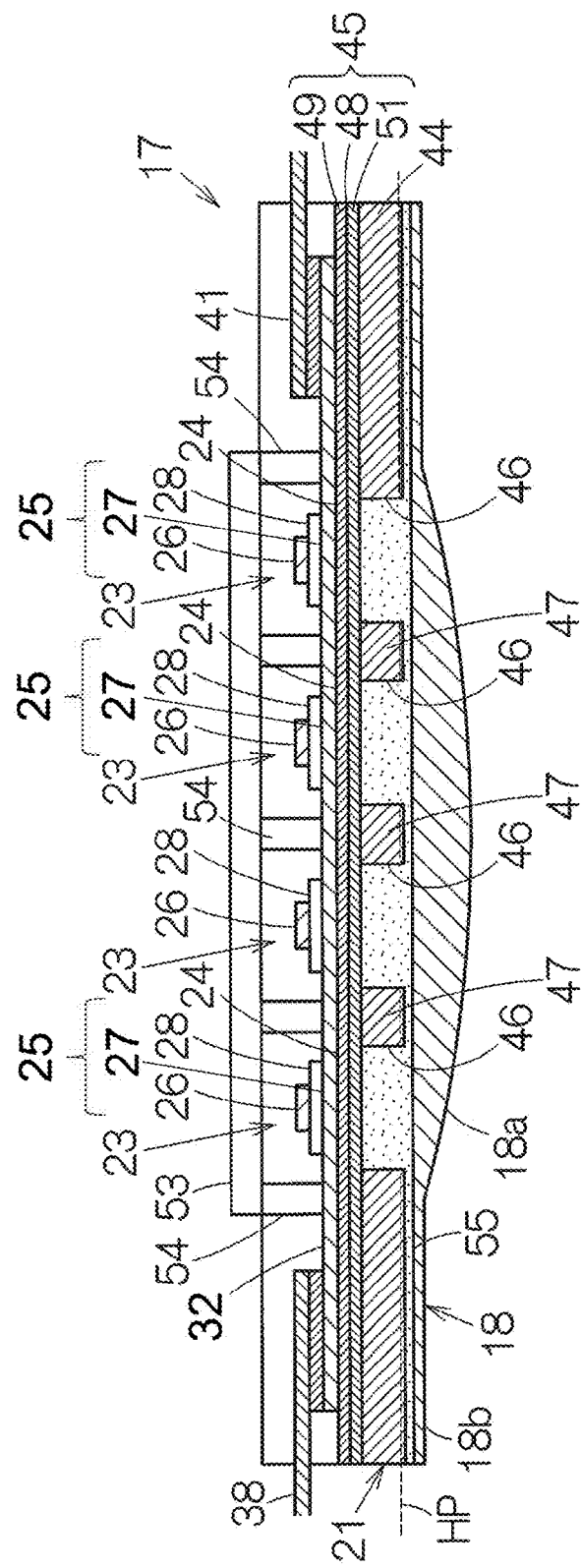
FIG. 3 is a cross-sectional view taken along line A-A in FIG. 1.

As shown in FIG. 3, the base 21 includes a device substrate 44 and a coating film 45. The coating film 45 is formed over the entire surface of the device substrate 44. The device substrate 44 may be formed of, for example, silicon (Si). In the device substrate 44, an opening 46 is formed for each element 23. The openings 46 are arranged in an array in the device substrate 44. The outline of a region where the openings 46 are arranged corresponds to the outline of the element array 22.

A partitioning wall 47 is disposed between every two adjacent openings 46. Adjacent openings 46 are separated from each other by the partitioning walls 47. The wall thickness of the partitioning walls 47 corresponds to the spacing between the openings 46. Each partitioning wall 47 defines two wall surfaces within planes that extend parallel to each other. The wall thickness corresponds to the distance between the two wall surfaces. That is to say, the wall thickness can be defined by the length of a normal line that extends between the wall surfaces orthogonally to the wall surfaces.

The coating film 45 includes a moisture-resistant layer (first layer) 48, a rigid film (second layer) 49, and a protective film (third layer) 51. The coating film 45 forms the vibration film 24 corresponding to the outline of each opening 46. The vibration films 24 refer to those portions of the coating film 45 that face the respective openings 46 and that can thus vibrate in the thickness direction of the device substrate 44. The moisture-resistant layer 48 is formed of a material having lower water permeability than at least silicon oxide. The moisture-resistant layer 48 physically isolates the piezoelectric elements 25 from the spaces within the respective openings 46. The moisture-resistant layer 48 is continuous between adjacent openings 46. Here, alumina ($Al_2O_3$) is used for the moisture-resistant layer 48. It is preferable that a material containing at least any of $Al_2O_3$, TaOx, and HfOx as a main component is used for the moisture-resistant layer 48. To obtain even higher moisture-resistance, it is preferable that the moisture-resistant layer 48 is formed of only at least any of $Al_2O_3$, TaOx, and HfOx.

The rigid film 49 is in close contact with a surface of the moisture-resistant layer 48 that receives the piezoelectric elements 25. The moisture-resistant layer 48 continuously and evenly extends over the entire surface of the rigid film 49. The rigid film 49 is formed of a material having a larger toughness value than the material of which the moisture-resistant layer 48 is formed. The toughness value can be measured as the value of KIC in conformity with, for example, an IF method specified by JIS R 1607-1990. The rigid film 49 has a larger toughness value than at least silicon oxide ($SiO_2$), silicon carbide (SiC), silicon nitride ($Si_3N_4$), and alumina ($Al_2O_3$). For example, materials containing, as a main component, zirconium oxide ($ZrO_2$) or stabilized zirconium containing Y (yttrium) or Ca (calcium) are preferable as the above-described material having strong toughness. To obtain an even higher toughness value, the rigid film 49 is more preferably formed of only $ZrO_2$ or stabilized zirconium. The film thickness of the rigid film 49 can be determined based on the resonance frequency of the vibration films 24.

The protective film 51 is in close contact with a surface of the moisture-resistant layer 48 on a side opposite to the surface that is in close contact with the rigid film 49. The protective film 51 closes the openings 46. The rigid film 49 and the moisture-resistant layer 48 are supported by the protective film 51. The protective film 51 is formed of a material having an etching rate that is different from the etching rate of the material for the device substrate 44 with respect to a specific etching solution. Here, a material containing, for example, silicon oxide ($SiO_2$) as a main component is preferable for the protective film 51. Furthermore, to stabilize the etching rate, it is preferable that the protective film 51 is formed of only $SiO_2$. The moisture-resistant layer 48 formed of alumina is sandwiched between the protective film 51 and the rigid film 49. Alumina serves to reliably bring the rigid film 49 formed of zirconium oxide into close contact with the protective film 51 formed of silicon oxide. The rigid film 49 and the protective film 51 are thus integrated together.

The first electric conductors 29 (top electrodes 26), the piezoelectric films 28, and the second electric conductors 32 (bottom electrodes 27) are sequentially laminated on the surface of the vibration film 24. The piezoelectric films 28 can be formed of, for example, lead zirconate titanate (PZT). Other piezoelectric materials may also be used for the piezoelectric films 28. The piezoelectric films 28 cover at least a portion of the respective bottom electrodes 27 and at least a portion of the respective vibration films 24. The top electrodes 26 cover at least a portion of the respective piezoelectric films 28. Here, the piezoelectric films 28 completely cover the surface of the respective second electric conductors 32 underneath the first electric conductors 29. The piezoelectric films 28 can serve to avoid short-circuiting between the first electric conductors 29 and the second electric conductors 32.

On the surface of the device substrate 44, a backing material 53 is attached over the coating film 45. The backing material 53 forms a space between the backing material 53 and the surface of the coating film 45. The piezoelectric elements 25 are arranged within that space. The backing material 53 is supported on the surface of the coating film 45 via wall materials 54. The wall materials 54 maintain a certain distance between the backing material 53 and the surface of the coating film 45. The wall materials 54 are supported by the device substrate 44 outside the outlines of the openings 46.

An acoustic matching layer 55 is laminated on a back surface of the device substrate 44 on the back side of the surface. The acoustic matching layer 55 covers the back surface of the device substrate 44 and is also disposed within the openings 46. The acoustic matching layer 55 comes into contact with the vibration film 24 within each opening 46. The acoustic matching layer 55 is in close contact with the vibration film 24 with no gap left therebetween. For example, a silicone resin film can be used for the acoustic matching layer 55. The acoustic impedance of the partitioning walls 47 is larger than the acoustic impedance of the acoustic matching layer 55.

An acoustic lens 18 is laminated on the acoustic matching layer 55. The acoustic lens 18 is in close contact with a surface of the acoustic matching layer 55 with no gap left therebetween. The partial cylindrical surface 18a of the acoustic lens 18 has generating lines that are parallel to the second electric conductors 32. The curvature of the partial cylindrical surface 18a is determined in accordance with the focus position of ultrasonic waves emitted from a single row of elements 23 connected to a single second electric conductor 32.

(3) Operation of Ultrasonic Diagnostic Apparatus

Next, the operation of the ultrasonic diagnostic apparatus 11 will be briefly described. To transmit ultrasonic waves, a pulse signal is supplied to the piezoelectric elements 25. The pulse signal is supplied to the elements 23 on a row-by-row basis through the bottom electrode terminals 35 and 37 and the top electrode terminals 34 and 36. In each element 23, an electric field acts on the piezoelectric film 28 between the bottom electrode 27 and the top electrode 26. The piezoelectric film 28 vibrates ultrasonically. The vibration of the piezoelectric film 28 is transferred to the vibration film 24. Thus, the vibration film 24 vibrates ultrasonically. The ultrasonic vibration of the vibration film 24 propagates through the acoustic matching layer 55. The ultrasonic vibration is transferred from the acoustic matching layer 55 to the acoustic lens 18 and is then emitted from the acoustic lens 18. As a result, a desired ultrasonic beam is emitted toward an object (for example, the interior of a human body).

Reflected waves of the ultrasonic waves propagate through the acoustic lens 18 and the acoustic matching layer 55 and then vibrate the vibration film 24. The ultrasonic vibration of the vibration film 24 ultrasonically vibrates the piezoelectric film 28 at a desired frequency. A voltage is output from the piezoelectric element 25 in accordance with the piezoelectric effect of the piezoelectric element 25. In each element 23, a potential is generated between the top electrode 26 and the bottom electrode 27. The generated potentials are output from the bottom electrode terminals 35 and 37 and the top electrode terminals 34 and 36 as electric signals. The ultrasonic waves are detected in this manner.

Ultrasonic waves are repeatedly transmitted and received. As a result, a linear scan or a sector scan is achieved. When the scan is completed, an image is formed based on digital signals of the output signals. The image thus formed is displayed on the screen of the display panel 15.

Generally, to form an ultrasonic image, the ultrasonic probe 13 is pressed against a subject. At this time, an acoustic coupling material having fluidity is present between the subject and the acoustic lens 18. For example, water can be used as the acoustic coupling material. The acoustic coupling material serves to establish acoustic matching between the subject and the acoustic lens 18, and thus reflection of ultrasonic waves at an interface therebetween can be prevented.

To transmit ultrasonic waves, the vibration film 24 vibrates ultrasonically. When vibrating, the vibration film 24 deforms. Since the rigid film 49 of the vibration film 24 has strong toughness, even when the rigid film 49 is subjected to deformation during the vibration, the occurrence of damage to or cracking in the surface of the rigid film 49 is prevented. Since the moisture-resistant layer 48 is in close contact with the surface of this rigid film 49, the continuity of the moisture-resistant layer 48 is maintained. Thus, the moisture-resistant ability is maintained on the surface of the vibration film 24. The piezoelectric elements 25 are isolated from water and moisture that enter the spaces in the respective openings 46. The piezoelectric elements 25 can be reliably protected against water and moisture.

At this time, the openings 46 are closed by the protective film 51. The protective film 51 is present between the device substrate 44 and the moisture-resistant layer 48 along the edge of each opening 46. Water and moisture penetrate the protective film 51. Here, since the moisture-resistant layer 48 extends continuously, the penetration of water and moisture is reliably blocked by the moisture-resistant layer 48. Also, a situation in which water and moisture go around the moisture-resistant layer 48 and reach the piezoelectric elements 25 is reliably avoided. Thus, the piezoelectric elements 25 are reliably protected against water and moisture.

As will be described later, to form the openings 46, the device substrate 44 is subjected to an etching process. Since the device substrate 44 and the protective film 51 have different etching rates, the protective film 51 functions as an etching stop layer. Thus, the vibration film 24 having a specific thickness is reliably secured.

(4) Method for Manufacturing Ultrasonic Device

Figure 4:
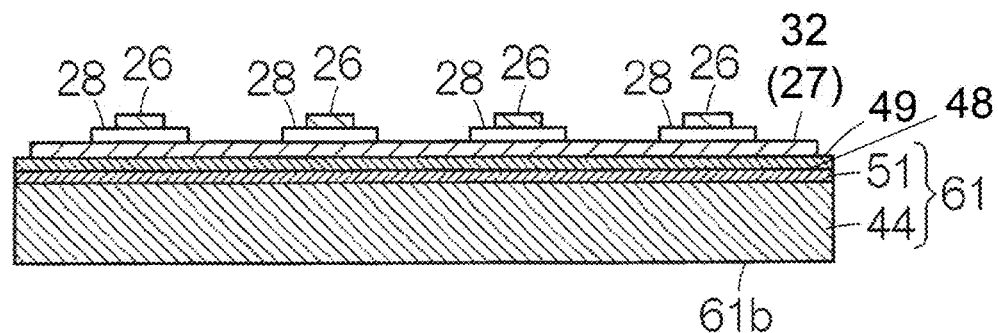
FIG. 4 is an enlarged cross-sectional view schematically showing steps up to formation of piezoelectric elements, of a method for manufacturing the ultrasonic device.

Next, a method for manufacturing the ultrasonic device 17 will be briefly described. As shown in FIG. 4, a substrate 61 is prepared. The substrate 61 may be formed of, for example, silicon. For example, heat treatment is applied to a surface of the substrate 61, so that an oxide film is formed. The film thickness of the oxide film may be set at, for example, about 400 nm. The silicon of the substrate 61 is oxidized and forms silicon oxide. The oxide film has a uniform film thickness. In this manner, the device substrate 44 and the protective film 51 are formed from the substrate 61.

An alumina layer is formed over the entire surface of the protective film 51. To form the alumina layer, an ALCVD method (atomic layer chemical vapor deposition method) may be used. The film thickness of the alumina layer may be set at, for example, about 20 nm. Thus, the moisture-resistant layer 48 is formed on the surface of the protective film 51.

Subsequently, a zirconium oxide layer is formed on the surface of the alumina layer. To form the zirconium oxide layer, a zirconium film is formed on the surface of the alumina layer. To form the film, sputtering may be used. The film thickness of the zirconium film may be set at, for example, about 800 nm. When the temperature during film formation is set to be equal to or lower than room temperature, crystal grains of the zirconium film are made minute. Oxidation treatment is applied to the zirconium film. The oxidation treatment may be performed in air using RTA (rapid thermal annealing) and furnace annealing. In RTA, oxidation treatment is performed at 900 degrees centigrade for 10 seconds. After that, in furnace annealing, oxidation treatment is performed at 850 degrees centigrade for one hour. As a result, a zirconium oxide film having a film thickness of 1200 nm is obtained. In this manner, the rigid film 49 is formed.

After that, the piezoelectric elements 25 are formed on the surface of the rigid film 49. For example, a material layer made of an electrically conductive material is formed over the entire surface of the zirconium oxide film. For example, sputtering may be used to form the material layer. The material layer is formed to have a uniform film thickness. A photoresist pattern is formed on the surface of the material layer. The pattern defines the shape of the second electric conductors 32. Etching is performed from the surface of the material layer. As a result, the second electric conductors 32 are formed from the material layer. Similarly, the piezoelectric films 28 and the top electrodes 26 (first electric conductors 29) are formed on the surface of the rigid film 49.

Figure 5:
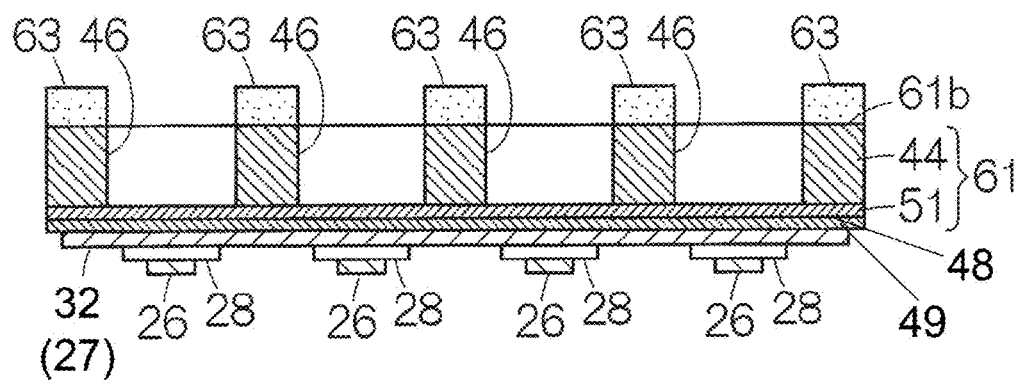
FIG. 5 is an enlarged cross-sectional view schematically showing a step of forming openings of the method for manufacturing the ultrasonic device.

After the piezoelectric elements 25 as well as the first electric conductors 29, the second electric conductors 32, the top electrode terminals 34 and 36, and the bottom electrode terminals 35 and 37 are formed in the above-described manner, as shown in FIG. 5, the openings 46 are formed in the device substrate 44 from a back surface 61*b* of the substrate 61. To form the openings 46, the back surface 61*b* of the device substrate 44 is subjected to an etching process. A pattern of a photoresist 63 is formed on the back surface 61*b* of the substrate 61. The pattern defines the shape of the outlines of the openings 46. In accordance with the etching process, the back surface 61*b* of the substrate 61 outside the photoresist 63 is engraved. At this time, etching is stopped at the protective film 51 as a result. The rigid film 49 and the moisture-resistant layer 48 are isolated from the etching solution by the protective film 51. The openings 46 are thus formed in the device substrate 44. The vibration film 24 is thus established.

Figure 6:
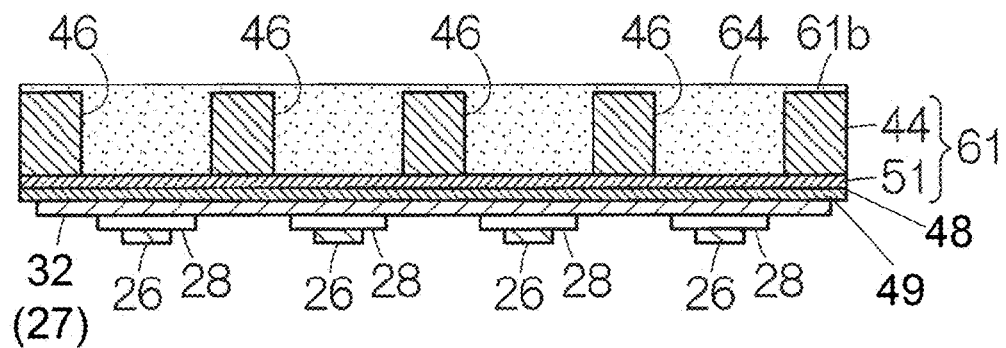
FIG. 6 is an enlarged cross-sectional view schematically showing a step of pouring a material for an acoustic matching layer of the method for manufacturing the ultrasonic device.

After that, as shown in FIG. 6, the material 64 for the acoustic matching layer 55 in fluid form is poured into the openings 46. Since the material 64 has fluidity, the spaces within the openings 46 are filled with the material 64. The material 64 is evenly in contact with the protective film 51. Here, the material 64 in fluid form spreads uniformly over the back surface 61*b* of the substrate 61. Thus, a flat surface of the material 64 extends over the entire back surface 61*b* of the substrate 61.

Figure 7:
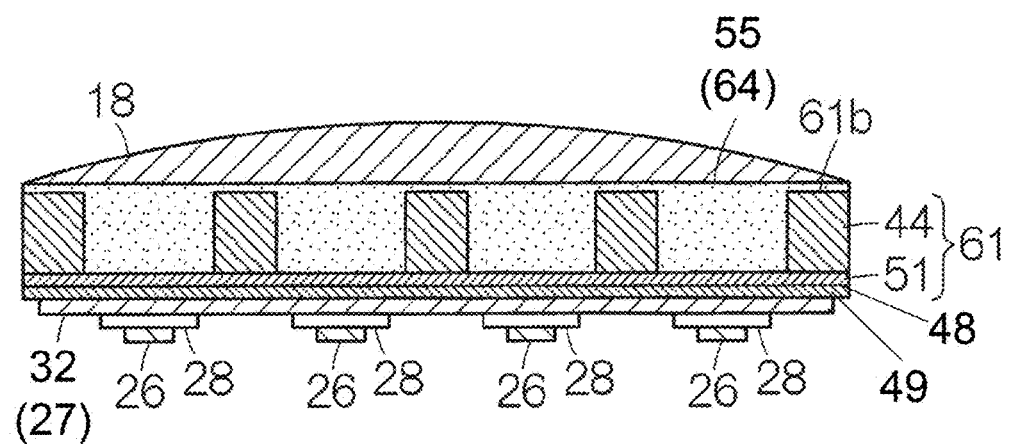
FIG. 7 is an enlarged cross-sectional view schematically showing a step of allowing adhesion of an acoustic lens of the method for manufacturing the ultrasonic device.

As shown in FIG. 7, the material 64 in fluid form that has been poured is covered with the acoustic lens 18. Since the material 64 has fluidity, the material 64 is evenly in contact with the acoustic lens 18. After that, hardening treatment is applied to the fluid. As the fluid hardens, the acoustic matching layer 55 is established. The acoustic lens 18 is allowed to adhere to the acoustic matching layer 55. The acoustic matching layer 55 is reliably brought into close contact with the vibration film 24 and the acoustic lens 18. As the close adhesion is achieved, reliable propagation of ultrasonic waves is established.

After that, the first wiring board 38 and the second wiring board 41 are joined to the device substrate 44. After the first wiring board 38 and the second wiring board 41 are mounted, the backing material 53 is joined to the surface of the substrate 61. In this manner, the ultrasonic device 17 is manufactured.

The piezoelectric films 28 are in contact with portions of the rigid film 49. The rigid film 49 separates the piezoelectric films 28 from the protective film 51 formed of silicon oxide. Zirconium oxide is passivated, and therefore lead in the piezoelectric films 28 does not diffuse toward the protective film 51 formed of silicon oxide. If PZT of the piezoelectric films 28 comes into direct contact with the protective film 51 formed of silicon oxide, lead in the PZT easily reacts with silicon, and thus the lead diffuses toward the protective film 51, resulting in breakage of the PZT.

Figure 8:
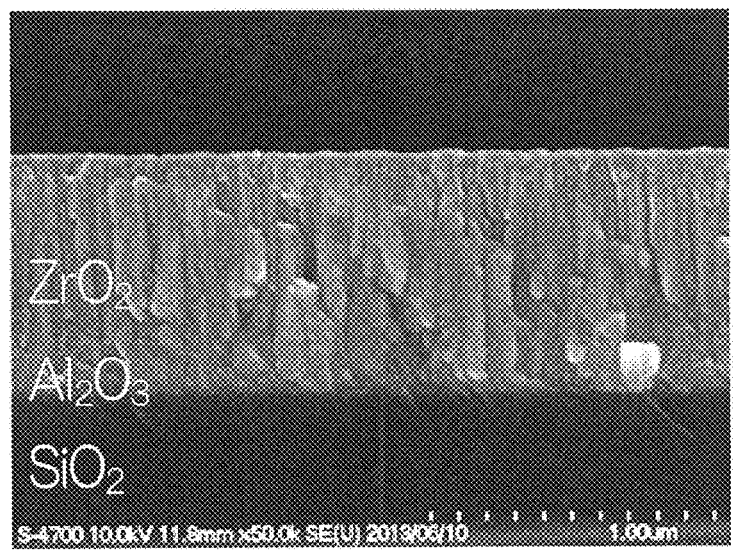
FIG. 8 is an electron micrograph showing a cross section of a laminate of a zirconium oxide film, an alumina layer, and a silicon oxide film.

FIG. 8 shows an electron micrograph of a laminate of a zirconium oxide film, an alumina layer, and a silicon oxide film. The layered structure of this laminate corresponds to the rigid film 49, the moisture-resistant layer 48, and the protective film 51. The laminate was formed in the same manner as the above-described manufacturing of the rigid film 49, the moisture-resistant layer 48, and the protective film 51. To take an electron micrograph, the laminate was cut along a cross section perpendicular to the film surface. It can be seen that the rigid film 49 is in close contact with the protective film 51 with no gap left therebetween.

Figure 9:
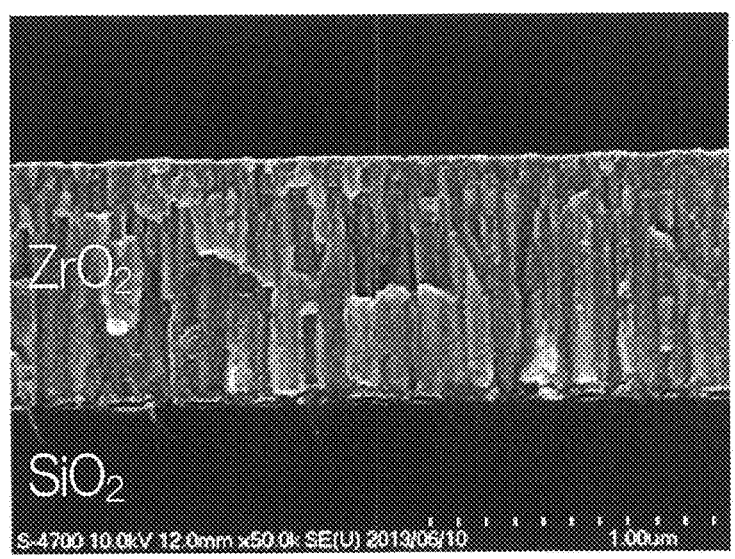
FIG. 9 is an electron micrograph showing a cross section of a zirconium oxide film and a silicon oxide film according to a comparative example.

FIG. 9 shows an electron micrograph of a zirconium oxide film and a silicon oxide film according to a comparative example. Except that the moisture-resistant layer 48 was omitted, the laminate was formed in same manner as described above. After a zirconium film was formed on the surface of the silicon oxide film, oxidation treatment was applied to the zirconium film by RTA and furnace annealing. As is clear from FIG. 9, in the comparative example, gaps were observed in places between the zirconium oxide film and the silicon oxide film. It was confirmed that if the zirconium oxide film is directly formed on the silicon oxide film without forming the alumina layer, the adhesion of the zirconium oxide film decreases.

Figure 10:
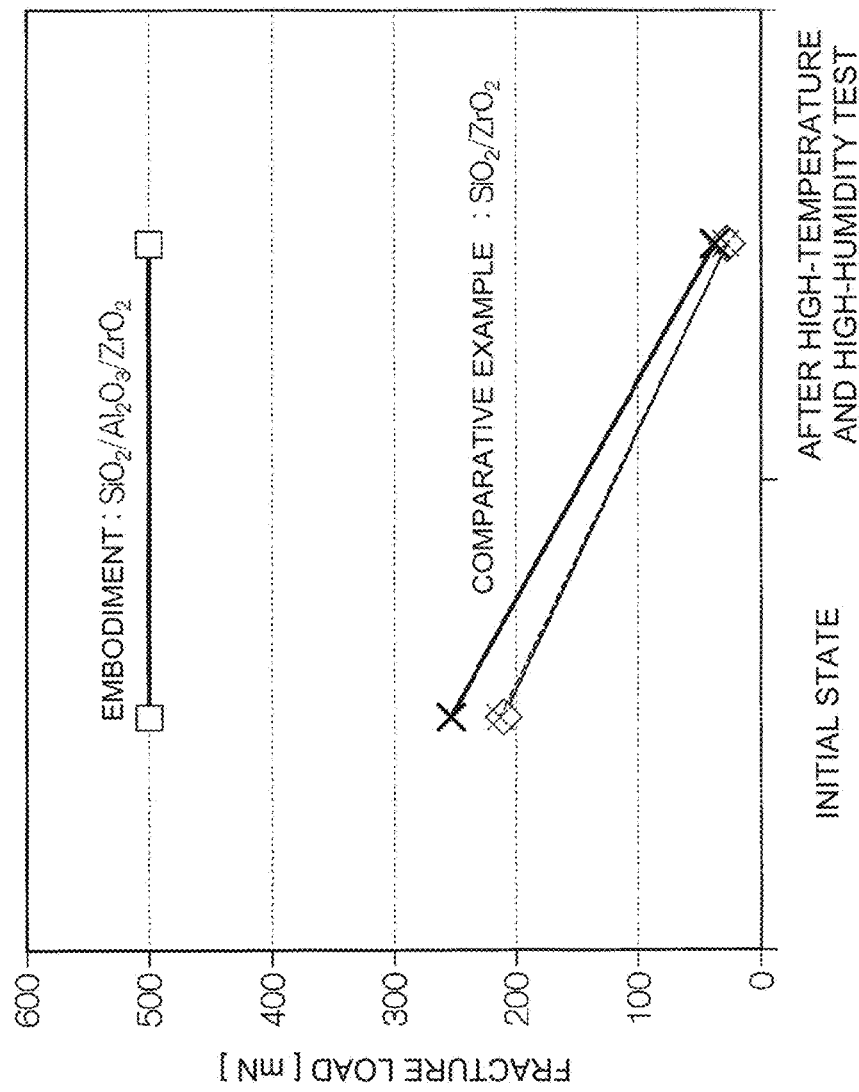
FIG. 10 is a graph showing an adhesive force of a zirconium oxide film.

The inventor of the embodiment evaluated the adhesive force of a zirconium oxide film. To perform the evaluation, a laminate of a zirconium oxide film, an alumina layer, and a silicon oxide film was prepared in the same manner as described above. Detachment of the zirconium oxide film was observed on a scratch tester. Detachment was observed in an initial state and after a high-temperature and high-humidity test. To perform the evaluation, a comparative example was prepared in the same manner as described above. In the comparative example, a zirconium oxide film was directly formed on the surface of a silicon oxide film. As a result of the observation, it was confirmed that, as shown in FIG. 10, the adhesive force of the zirconium oxide film is increased by the presence of the intervening alumina layer. Moreover, it was found that although the adhesive force is reduced to half or less by a high-temperature and high-humidity environment in the comparative example, the adhesive force is maintained irrespective of the effect of a high-temperature and high-humidity environment in the present embodiment.

(5) Configuration of Ultrasonic Device According to Second Embodiment

Figure 11:
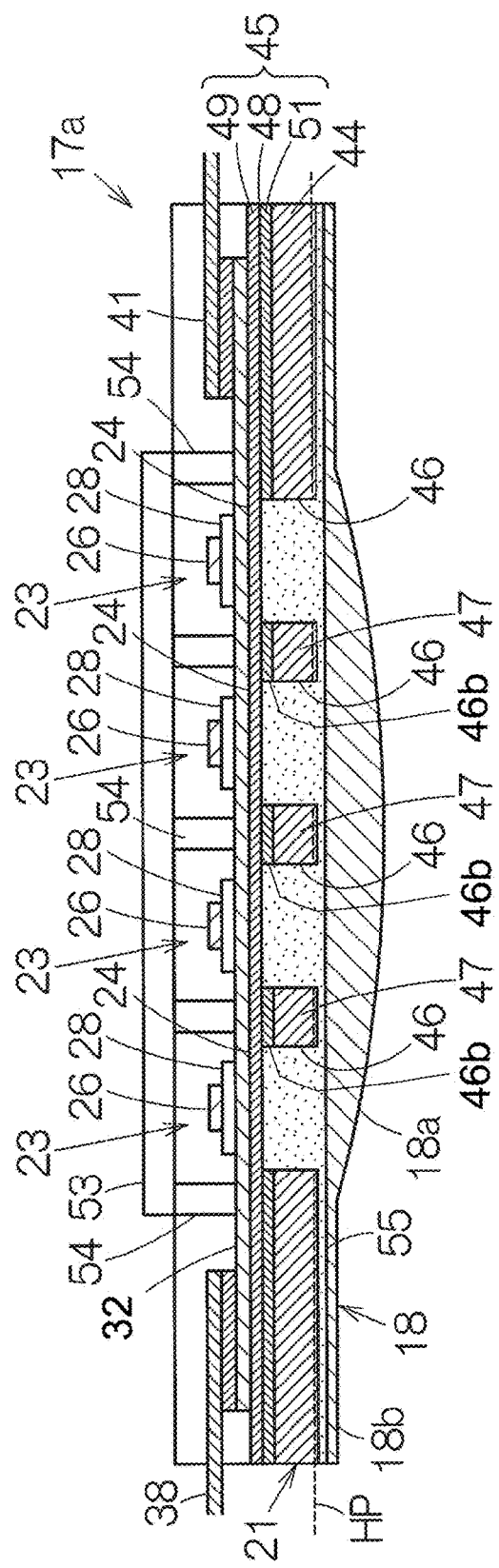
FIG. 11 is an enlarged plan view of an ultrasonic device according to a second embodiment.

FIG. 11 schematically shows the configuration of an ultrasonic device 17a according to a second embodiment. In the second embodiment, openings 46b are formed in the protective film 51 so as to correspond to the respective openings 46 in the device substrate 44. These openings 46b are continuous with the respective openings 46 in the device substrate 44. Although the protective film 51 covers regions of the surface of the device substrate 44 that are located between the openings 46, 46b, the openings 46, 46b are closed by the moisture-resistant layer 48. On the inside of the outlines of the respective openings 46, 46b, the moisture-resistant layer 48 is in direct contact with the acoustic matching layer 55. The other structures are the same as those of the ultrasonic device 17 according to the above-described first embodiment.

To manufacture the ultrasonic device 17a, in the same manner as described above, the protective film 51, the moisture-resistant layer 48, and the rigid film 49 are laminated on the surface of the device substrate 44. The piezoelectric elements 25, the first electric conductors 29, the second electric conductors 32, the top electrode terminals 34 and 36, and the bottom electrode terminals 35 and 37 are formed on the surface of the rigid film 49. The openings 46 are formed in the device substrate 44 from the back surface 61b of the substrate 61. Etching is stopped at the protective film 51. After that, an etching process is performed again with respect to the protective film 51 formed of silicon oxide. Thus, the openings 46b that are continuous with the respective openings 46 of the device substrate 44 are formed in the protective film 51.

Although some embodiments of the invention have been described in detail above, a person skilled in the art will readily understand that various modifications may be made without substantially departing from the novel teachings and the effects of the invention. Therefore, such modifications are entirely included within the scope of the invention. For example, any term described at least once together with a broader or synonymous different term in the specification or the drawings may be replaced by the different term at any place in the specification or the drawings. Moreover, the configurations and operations of the ultrasonic diagnostic apparatus 11, the display panel 15, the ultrasonic devices 17, 17a, the elements 23, and the like are not limited to those described in the foregoing embodiments, but may be modified in various manners. In addition, the configurations of the rigid film 49, the piezoelectric elements 25, and the moisture-resistant layer 48 (and the protective film 51) may be applied to MEMS devices such as an acceleration sensor, a gyro sensor, an inkjet printer head, and a vibration power-generating element.

According to at least one aspect of the embodiment, it is possible to provide a piezoelectric device that can reliably protect a piezoelectric element against water and moisture.

An aspect of the embodiment is directed to a piezoelectric device including a base having an opening, a vibration film that closes the opening, and a piezoelectric element supported by the vibration film. The vibration film includes a first layer that is formed of a material having lower water permeability than silicon oxide and a second layer that is formed in close contact with the first layer and that has a larger toughness value than the material of which the first layer is formed.

The vibration film vibrates ultrasonically. When vibrating, the vibration film deforms. Since the second layer of the vibration film has strong toughness, even if the second layer is subjected to deformation during the vibration, the occurrence of damage to or cracking in the surface of the second layer is prevented. Since the first layer is in close contact with the surface of this second layer, the continuity of the first layer is maintained. Thus, the moisture-resistant ability is maintained on the surface of the vibration film. The piezoelectric element is isolated from water and moisture that may enter the space within the opening. The piezoelectric element can thus be reliably protected against water and moisture.

The base may have a plurality of the openings, and the first layer may be continuous between adjacent ones of the openings. Since the first layer continuously extends, the piezoelectric element is reliably protected against water and moisture.

The vibration film may include a third layer that is provided closer to the opening than the first layer and the second layer are and that has an etching rate different from an etching rate of a material for the base. To form the opening, the base is subjected to an etching process. Since the base and the third layer have different etching rates, the third layer functions as an etching stop layer. Thus, the vibration film having a specific thickness is reliably secured.

The second layer can be formed to contain zirconium oxide ($ZrO_2$). Zirconium oxide has higher toughness than at least silicon nitride ($Si_3N_4$), silicon carbide (SiC), and alumina ($Al_2O_3$).

The first layer can be formed to contain at least any of alumina ($Al_2O_3$), tantalum oxide (TaOx), and hafnium oxide (HfOx). Alumina, tantalum oxide, and hafnium oxide have lower water permeability than at least silicon oxide ($SiO_2$).

The third layer can be formed to contain silicon oxide ($SiO_2$). For example, the base can be formed of silicon, and in that case, silicon oxide has an etching rate that is different from (slower than) the etching rate of silicon with respect to a specific etching solution.

It is possible that the second layer is formed of $ZrO_2$, the first layer is formed of $Al_2O_3$, and the first layer is formed in a position at which the first layer is sandwiched between the second layer and the third layer. $Al_2O_3$ serves to reliably bring the vibration film formed of $ZrO_2$ into close contact with the protective film formed of $SiO_2$.

An ultrasonic device can include the piezoelectric device. Thus, the piezoelectric device can be used in the ultrasonic device.

The ultrasonic device can be used in a state in which it is incorporated into a probe. At this time, it is sufficient if the probe includes the ultrasonic device and a housing that supports the ultrasonic device.

The ultrasonic device can be used in a state in which it is incorporated into an electronic apparatus. At this time, it is sufficient if the electronic apparatus includes the ultrasonic device and a processor that is connected to the ultrasonic device and that processes an output from the ultrasonic device.

The ultrasonic device can be used in a state in which it is incorporated into an ultrasonic imaging apparatus. At this time, it is sufficient if the ultrasonic imaging apparatus includes the ultrasonic device and a display device that displays an image generated based on an output from the ultrasonic device.

The entire disclosure of Japanese Patent Application No. 2014-155714 filed on Jul. 31, 2014 is expressly incorporated by reference herein.

General Interpretation Of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A piezoelectric device, comprising:
a base having at least one opening;
a vibration film that closes the opening; and
a piezoelectric element located on the vibration film,
the vibration film including a first layer and a second layer that is in close contact with the first layer,
the first layer having lower water permeability than silicon oxide, and
the second layer having a larger toughness value than the first layer.

2. The piezoelectric device according to claim 1, wherein the base has a plurality of openings including the opening, and the first layer is continuous between adjacent ones of the openings.

3. The piezoelectric device according to claim 1, wherein the vibration film further includes a third layer that is provided closer to the opening than the first layer and the second layer are and that has an etching rate different from an etching rate of the base.

4. The piezoelectric device according to claim 1, wherein the second layer contains $ZrO_2$.

5. The piezoelectric device according to claim 1, wherein the first layer contains at least one of $Al_2O_3$, TaOx, and HfOx.

6. The piezoelectric device according to claim 3, wherein the third layer contains $SiO_2$.

7. The piezoelectric device according to claim 6, wherein the second layer is formed of $ZrO_2$, the first layer is formed of $Al_2O_3$, and the first layer is arranged such that the first layer is sandwiched between the second layer and the third layer.

8. An ultrasonic device, comprising:
the piezoelectric device according to claim 1.

9. An ultrasonic device, comprising:
the piezoelectric device according to claim 2.

10. An ultrasonic device, comprising:
the piezoelectric device according to claim 3.

11. An ultrasonic device, comprising:
the piezoelectric device according to claim 4.

12. An ultrasonic device, comprising:
the piezoelectric device according to claim 5.

13. An ultrasonic device, comprising:
the piezoelectric device according to claim 6.

14. An ultrasonic device, comprising:
the piezoelectric device according to claim 7.

15. A probe, comprising:
the ultrasonic device according to claim 8; and
a housing that supports the ultrasonic device.

16. An electronic apparatus, comprising:
the ultrasonic device according to claim 8; and
a processor connected to the ultrasonic device and configured to process an output from the ultrasonic device.

17. An ultrasonic imaging apparatus, comprising:
the ultrasonic device according to claim 8; and
a display device configured to display an image generated based on an output from the ultrasonic device.

18. A piezoelectric device, comprising:
a base having an opening;
a protective film provided on the base;
a vibration film including a first layer and a second layer that are laminated on the protective film in an order of the first layer and the second layer; and
a piezoelectric element that is provided on the vibration film, the piezoelectric element being provided in a position at which the piezoelectric element overlaps the opening when viewed in a thickness direction of the base,
the first layer having lower water permeability than the protective film,
the second layer having a toughness value that is larger than a toughness value of the first layer.

* * * * *